United States Patent
Park et al.

(10) Patent No.: US 10,815,577 B2
(45) Date of Patent: Oct. 27, 2020

(54) METHOD AND APPARATUS FOR PREPARING REDUCTION PRODUCT OF CARBON DIOXIDE BY ELECTROCHEMICALLY REDUCING CARBON DIOXIDE

(71) Applicant: KOREA INSTITUTE OF ENERGY RESEARCH, Daejeon (KR)

(72) Inventors: Ki Tae Park, Sejong-si (KR); Soon Kwan Jeong, Sejong-si (KR); Hak Joo Kim, Daejeon (KR); Seong Pil Kang, Daejeon (KR); Min Hye Youn, Sejong (KR)

(73) Assignee: KOREA INSTITUTE OF ENERGY RESEARCH, Daejeon (KR)

( * ) Notice: Subject to any disclaimer, the term of this patent is extended or adjusted under 35 U.S.C. 154(b) by 216 days.

(21) Appl. No.: 15/744,327

(22) PCT Filed: Jul. 14, 2016

(86) PCT No.: PCT/KR2016/007639
§ 371 (c)(1),
(2) Date: Jan. 12, 2018

(87) PCT Pub. No.: WO2017/010814
PCT Pub. Date: Jan. 19, 2017

(65) Prior Publication Data
US 2018/0202056 A1    Jul. 19, 2018

(30) Foreign Application Priority Data

Jul. 14, 2015 (KR) .................. 10-2015-0099992

(51) Int. Cl.
*C25B 3/04* (2006.01)
*C25B 15/02* (2006.01)
(Continued)

(52) U.S. Cl.
CPC ............. *C25B 3/04* (2013.01); *B01D 53/326* (2013.01); *B01D 53/965* (2013.01); *C07C 51/15* (2013.01);
(Continued)

(58) Field of Classification Search
CPC ...................................... C25B 3/04
See application file for complete search history.

(56) References Cited

U.S. PATENT DOCUMENTS

2012/0171583 A1* 7/2012 Bocarsly ............ H01M 4/8657
                                                    429/413
2014/0346053 A1   11/2014 Deguchi et al.
(Continued)

FOREIGN PATENT DOCUMENTS

JP      2015-004120 A     1/2015
KR   10-2014-0073007 A    6/2014
(Continued)

OTHER PUBLICATIONS

Kriescher et al, A membrane electrode assembly for the electrochemical synthesis of hydrocarbons from CO2(g) and H2O(g), Electrochemistry Communications, vol. 50, Nov. 2014, pp. 64-68 (Year: 2014).*

(Continued)

*Primary Examiner* — Harry D Wilkins, III
(74) *Attorney, Agent, or Firm* — Birch, Stewart, Kolasch & Birch, LLP

(57) ABSTRACT

The present invention relates to a method and an apparatus of preparing a reduction product of carbon dioxide by electrochemically reducing carbon dioxide.
The present invention can prepare, in an energy-efficient manner, a reduction product of high-concentration carbon dioxide with high Faraday efficiency as in a liquid reduction reaction by producing the reduction product of carbon (Continued)

dioxide by supplying water or an electrolytic solution to an anode region; supplying humidified carbon dioxide gas having a second temperature higher than a first temperature to a cathode region within an electrochemical cell having the first temperature so as to supply the carbon dioxide gas which has been humidified to be in a condition where the relative humidity is greater than 100%, while applying a voltage between the anode region and the cathode region so as to generate hydrogen ions ($H^+$) in the anode region; and transporting the hydrogen ions to the cathode region through the electrolyte membrane, thereby electrochemically reducing the carbon dioxide gas.

18 Claims, 8 Drawing Sheets

(51) Int. Cl.

| | | |
|---|---|---|
| *C25B 11/04* | (2006.01) | |
| *B01D 53/32* | (2006.01) | |
| *B01D 53/96* | (2006.01) | |
| *C07C 51/15* | (2006.01) | |
| *C07C 53/06* | (2006.01) | |
| *C07C 53/10* | (2006.01) | |
| *C01B 32/50* | (2017.01) | |
| *C01B 32/40* | (2017.01) | |
| *B01D 3/06* | (2006.01) | |
| *B01D 53/14* | (2006.01) | |

(52) U.S. Cl.
CPC .............. *C07C 53/06* (2013.01); *C07C 53/10* (2013.01); *C25B 11/04* (2013.01); *C25B 15/02* (2013.01); *B01D 3/06* (2013.01); *B01D 53/1487* (2013.01); *C01B 32/40* (2017.08); *C01B 32/50* (2017.08)

(56) References Cited

U.S. PATENT DOCUMENTS

| | | | |
|---|---|---|---|
| 2016/0226090 A1* | 8/2016 | Sone | C25B 3/04 |
| 2017/0183789 A1* | 6/2017 | Matthews | C25B 13/08 |
| 2020/0063273 A1* | 2/2020 | Masel | B01J 19/245 |

FOREIGN PATENT DOCUMENTS

| | | | |
|---|---|---|---|
| KR | 10-2014-0138153 A | | 12/2014 |
| KR | 10-2015-0056627 A | | 5/2015 |
| WO | WO 2012/118065 A1 | | 9/2012 |
| WO | WO 2012/128148 A1 | | 9/2012 |
| WO | WO 2013/134418 A1 | | 9/2013 |
| WO | WO 2014/046791 A1 | | 3/2014 |
| WO | WO 2016-039999 | * | 3/2016 ............. C25B 13/00 |

OTHER PUBLICATIONS

Strip-Elgiloy Alloy, Elgiloy Specialty Metals obtained at https://www.elgiloy.com/strip-elgiloy-alloy/ on Jun. 11, 2020 (Year: 2020).*
Kriescher et al, A membrane electrode assembly for the electrochemical synthesis of hydrocarbons from CO2(g) and H2O(g), Electrochemistry Communications, vol. 50, Jan. 2015, pp. 64-68 (Year: 2015).*
International Search Report (PCT/ISA/210) issued in PCT/KR2016/007639, dated Dec. 8, 2016.
Kim et al., "Analysis on the effect of operating conditions on electrochemical conversion of carbon dioxide to formic acid", Elsevier, International Journal of Hydrogen Energy, vol. 39, Issue 29, Oct. 2, 2014, pp. 16506-16512.
Lee et al., "Sustainable production of formic acid by electrolytic reduction of gaseous carbon dioxide", Journal of Materials Chemistry A, vol. 3, 2015, pp. 3029-3034.
Written Opinion (PCT/ISA/237) issued in PCT/KR2016/007639, dated Dec. 8, 2016.

* cited by examiner

[FIG. 1A]
Limitation of Gas-Phase Reaction
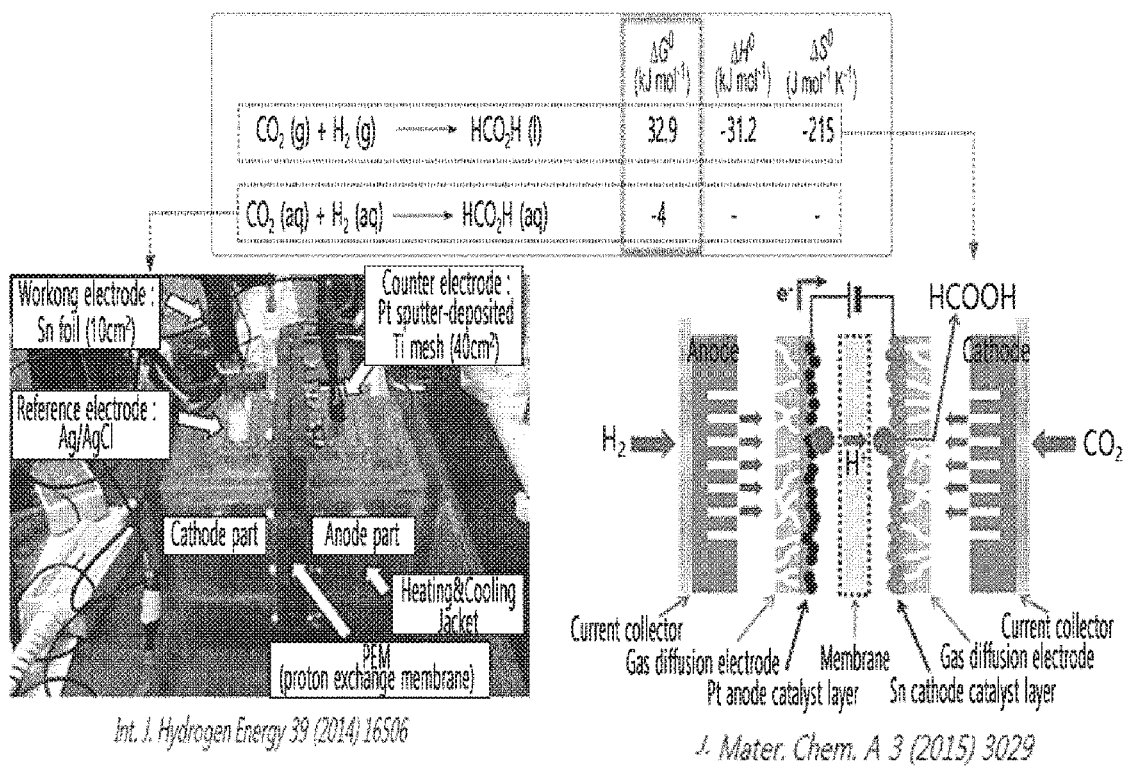
liquid-phase reaction
High Faradaic efficiency(>80%), but the concentration of products is at the level of a few hundred ppm (0.1% or less)
gas-phase reaction
Faradaic efficiency is 1/7 or less, but the concentration of products is at the level of a few tens mmol/L (0.1% or less)

[FIG. 1B]
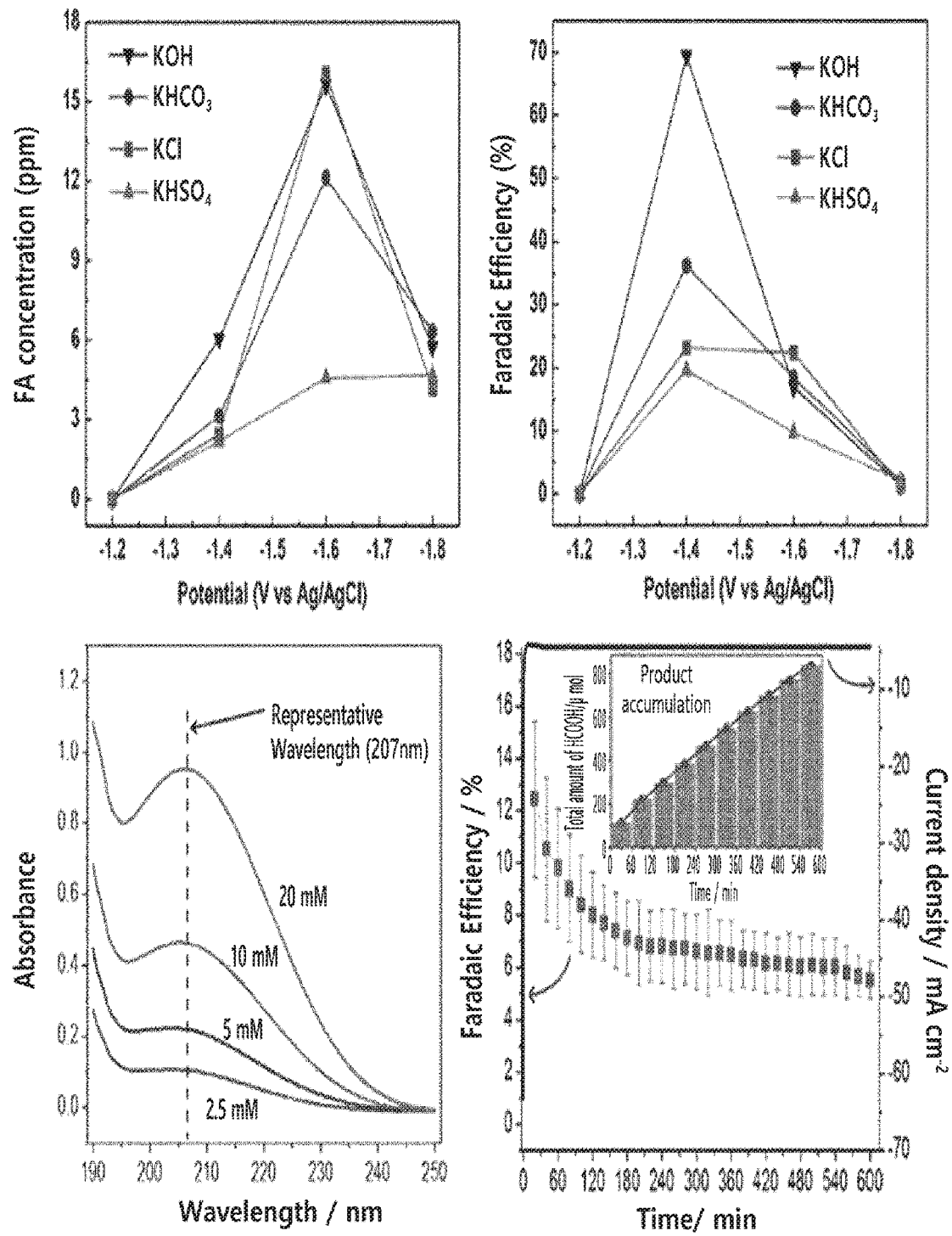

[FIG. 2]
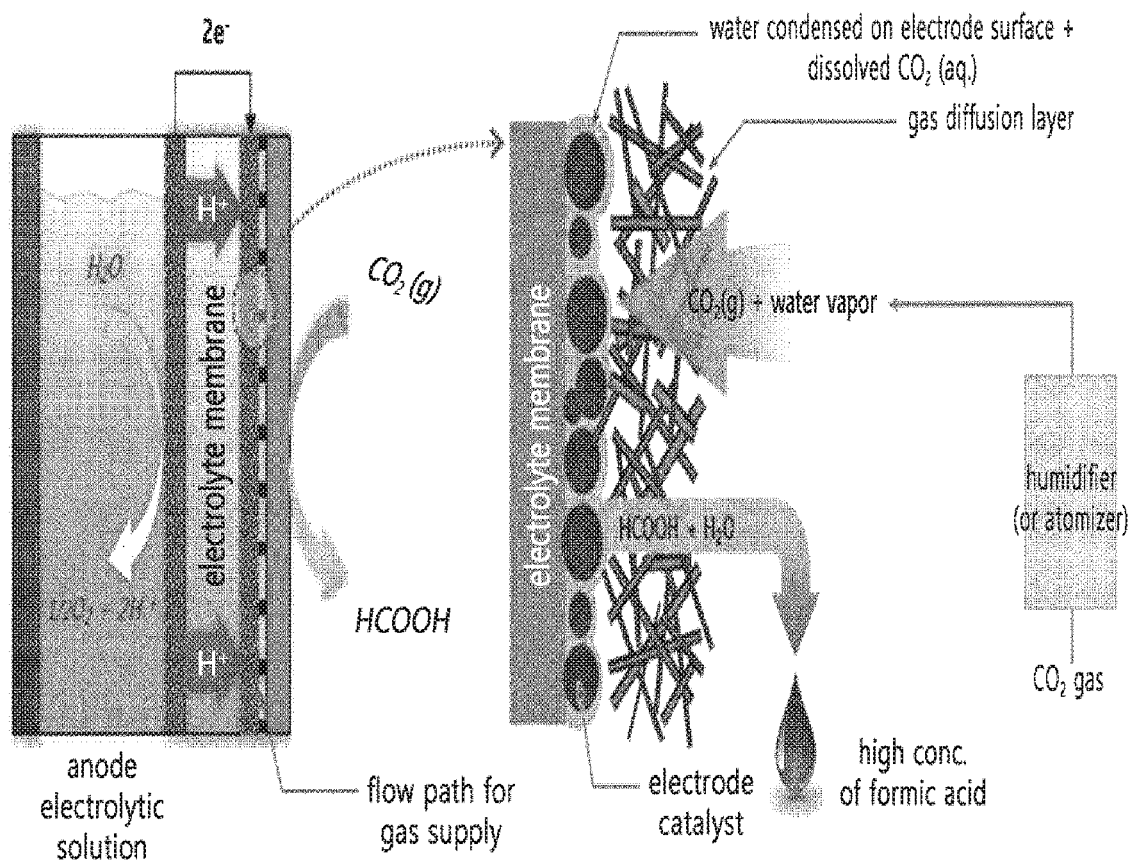

[FIG. 3]
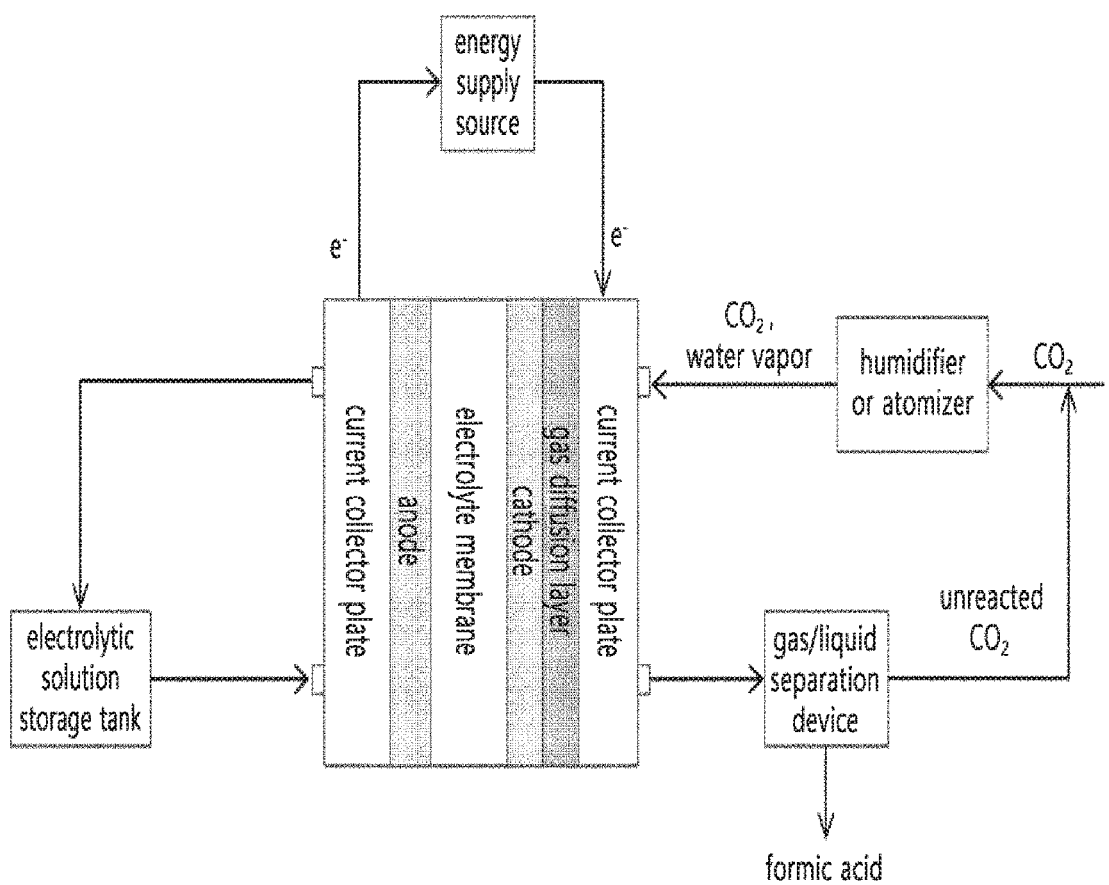

[FIG. 4]
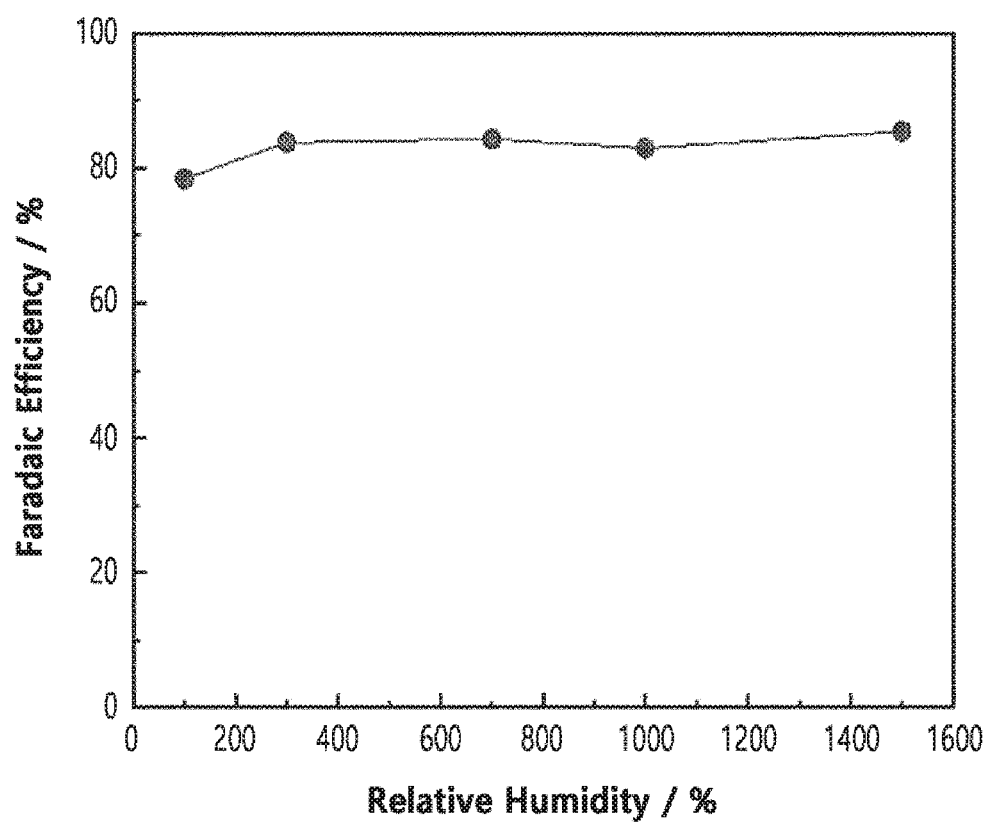

[FIG. 5]
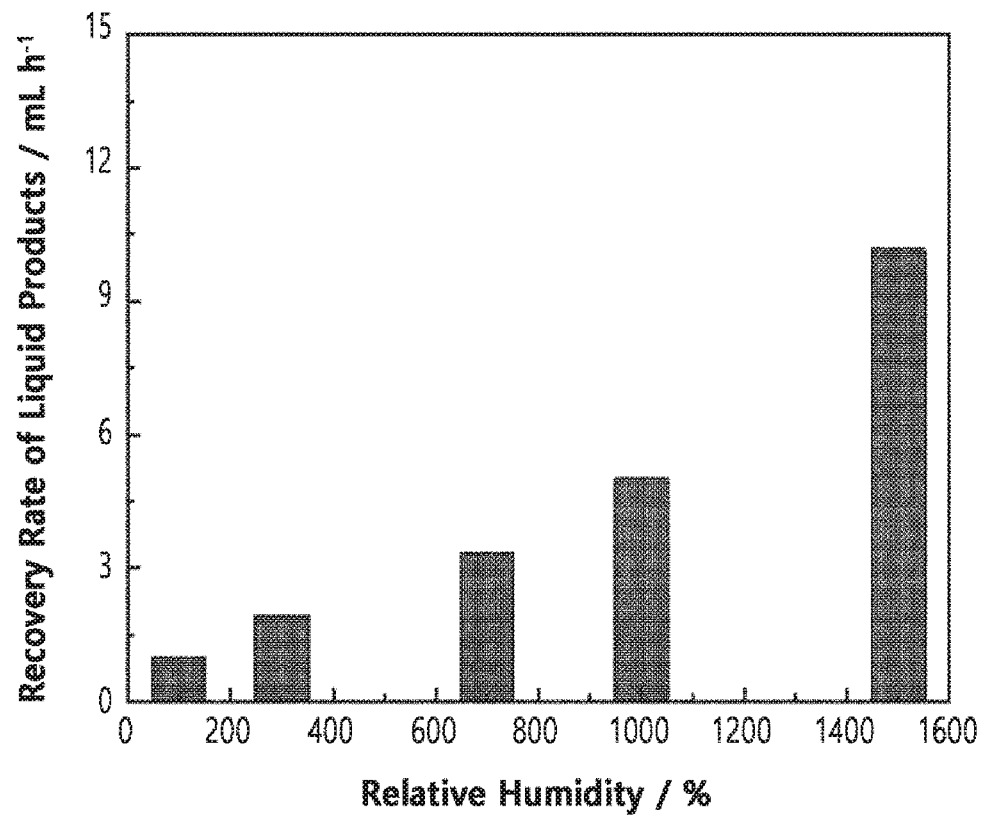

[FIG. 6]
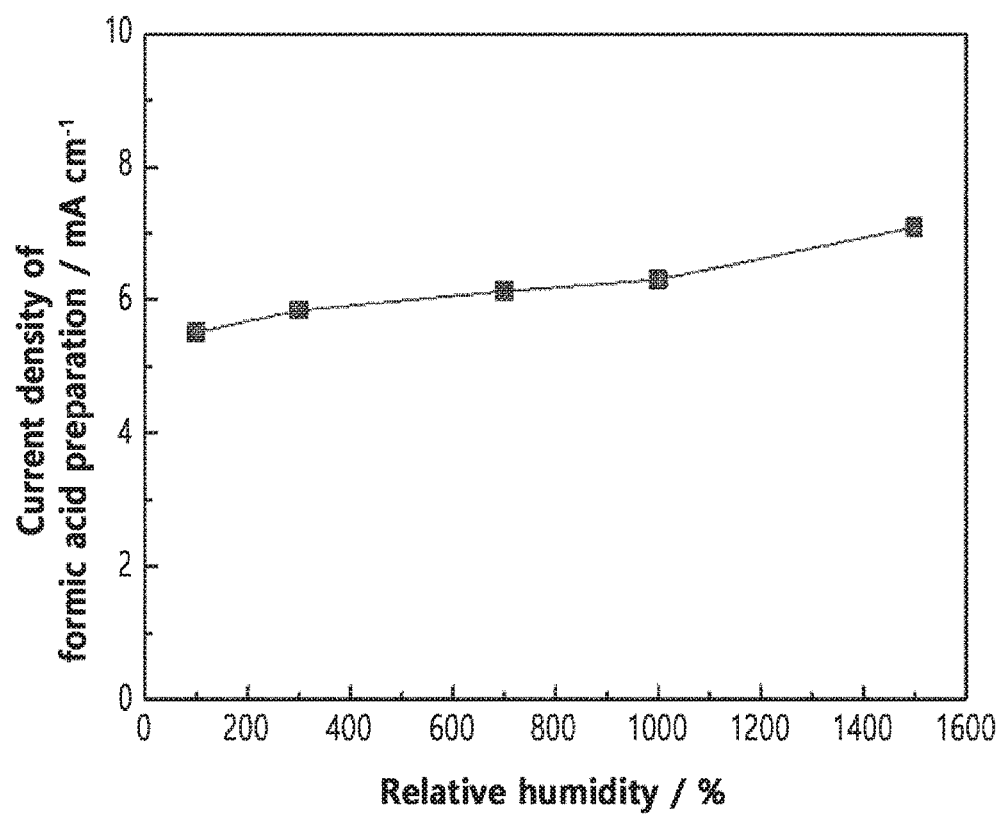

[FIG. 7]
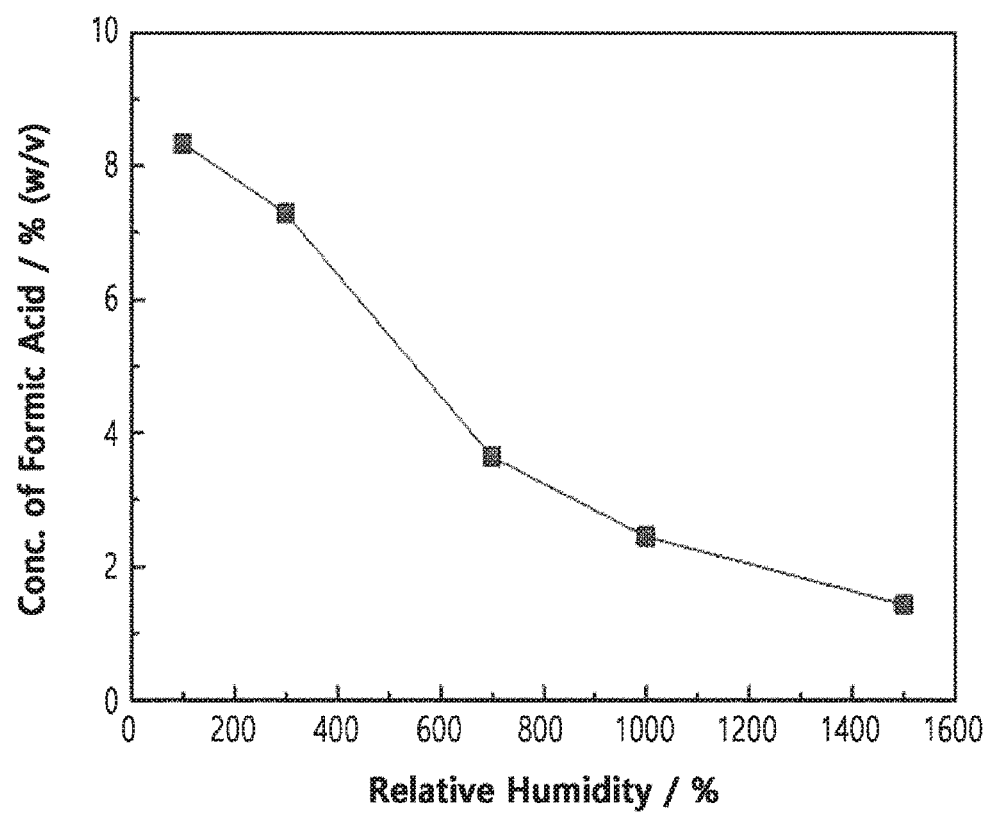

METHOD AND APPARATUS FOR PREPARING REDUCTION PRODUCT OF CARBON DIOXIDE BY ELECTROCHEMICALLY REDUCING CARBON DIOXIDE

TECHNICAL FIELD

The present invention relates to a method and apparatus of preparing a reduction product of carbon dioxide by electrochemically reducing carbon dioxide.

BACKGROUND ART

The way in which carbon dioxide is reduced electrochemically depends on the methods of ion exchange. Among these, the reduction of electrochemical carbon dioxide using a cation-exchange membrane causes the decomposition of water in the anode to generate oxygen, electrons, and hydrogen cations. At the cathode, carbon dioxide reacts with the electrons and hydrogen cations generated at the anode to cause a reduction reaction and is converted to a different material.

Among the reduction products of carbon dioxide, the product in liquid form has an advantage in that it has a higher energy density and is easier to handle than the product in gaseous form. In particular, formic acid has the advantage that it can be used in the synthesis of medicines or in the production processes of paper and pulp, and also has a higher price than other reduction products of carbon dioxide in liquid form. For this reason, formic acid has attracted much attention compared to other materials that can be formed by reducing carbon dioxide.

Generally, in the liquid-phase reduction reaction of carbon dioxide, Faradaic efficiency (or current efficiency) is higher than that of the gas-phase reduction reaction by more than 80%, but the product concentration is as low as several hundred ppm because the product is mixed with a liquid electrolyte (*Int. J. Hydrogen Energy* 39 (2014) 16506). As a result, the product has a very low value and the liquid-phase reaction requires separate separation and concentration processes.

Meanwhile, with regard to the Faradaic efficiency of the gas-phase reaction of carbon dioxide, the highest performance reported so far is 10% (*J. Mater. Chem. A*, 2015, 3, 3029). Additionally, the concentration of the product in the gas-phase reduction of carbon dioxide is also in the range of several mmol/L to several tens of mmol/L (at the level of thousands of ppm) and thus has a very low value as a product. Therefore, the gas-phase reduction reaction requires separate separation and concentration processes.

DISCLOSURE

Technical Problem

An object of the present invention is to provide an apparatus and method for preparing reduction products of carbon dioxide at high concentration and high Faradaic efficiency in an energy-efficient manner by electrochemically reducing carbon dioxide.

Technical Solution

A first aspect of the present invention provides a method of preparing a reduction product of carbon dioxide ($CO_2$) by electrochemically reducing carbon dioxide within an electrochemical cell, which comprises an anode, a cathode, and an electrolyte membrane which is disposed between the anode and the cathode to separate the anode region and the cathode region, and has a first temperature, comprising:

(1) supplying water or an electrolytic solution to the anode region;

(2) supplying a carbon dioxide gas which has been humidified in a condition where the relative humidity exceeds 100% by supplying a humidified carbon dioxide gas having a second temperature higher than the first temperature to the cathode region within the electrochemical cell having the first temperature; and (3) applying a voltage between the anode region and the cathode region to generate hydrogen ions ($H^+$) in the anode region, wherein the hydrogen ions move through the electrolyte membrane to the cathode region and then electrochemically reduce the carbon dioxide gas so as to produce a reduction product of carbon dioxide.

A second aspect of the present invention provides apparatus of preparing a reduction product of carbon dioxide ($CO_2$) by electrochemically reducing carbon dioxide, which includes:

an electrochemical cell, which comprises an anode; a cathode; and an electrolyte membrane which is disposed between the anode and the cathode to separate the anode region and the cathode region; an inlet of supplying water or an electrolytic solution to the anode region; and an inlet of supplying humidified carbon dioxide to the cathode region;

an energy supply source, which is operably linked to the anode and the cathode, and applies a voltage between the anode and the cathode to reduce the carbon dioxide in the cathode to a reduction product of the carbon dioxide; and a humidifier or atomizer, which is linked to the inlet for supplying humidified carbon dioxide to the cathode region and supplies humidified carbon dioxide to the cathode region, wherein water or an electrolytic solution is supplied to the anode region; a carbon dioxide gas which has been humidified in a condition where the relative humidity exceeds 100% is supplied by supplying the humidified carbon dioxide gas having a second temperature higher than a first temperature to the cathode region within the electrochemical cell having the first temperature; and a voltage is applied between the anode and the cathode to generate hydrogen ions ($H^+$) in the anode region, the hydrogen ions are transported to the cathode region through the electrolyte membrane, and electrochemically reduce the carbon dioxide gas and a reduction product of carbon dioxide is produced.

Hereinafter, the present invention will be described in detail.

The existing liquid-phase reaction of carbon dioxide has a Faradaic efficiency (or current efficiency) of 80% or higher, which is higher than that of the gas-phase reaction, but the product concentration is as low as several hundred ppm. Meanwhile, since the gas-phase reaction of carbon dioxide is a non-spontaneous reaction, energy efficiency is very low and the Faradaic efficiency is very low to the level of 10%.

The limitations of the gas-phase reaction can be explained thermodynamically as in FIG. 1. For example, while the reaction of reducing $CO_2$ dissolved in a liquid phase in the standard state to formic acid is a spontaneous reaction, the reaction of reducing $CO_2$ in the gas phase to formic acid is a non-spontaneous reaction and thus requires very much energy for the reaction. In the case of the previously-reported gas-phase reactions, the reactants at both electrodes are in the gas phase ($H_2/CO_2$).

The purpose of supplying these gas-phase reactants at both electrodes at 100% of relative humidity is only to prevent performance deterioration caused by dryness of the electrolyte membrane. Here, since the relative humidity does not exceed 100%, the phenomenon of water condensing in a liquid phase hardly occurs, and thus the reaction proceeds in a gas phase.

In the present invention, as shown in FIG. 2, it was found that reduction products of carbon dioxide can be prepared at high concentration and high Faradaic efficiency in an energy-efficient manner as in the liquid-phase reduction reaction: by supplying water or an electrolytic solution to the anode region; applying a voltage between the anode and the cathode to induce a reduction reaction of the carbon dioxide gas under the condition where the relative humidity exceeds 100% by supplying humidified carbon dioxide gas having a second temperature higher than a first temperature to the cathode region within the electrochemical cell having the first temperature; allowing the water in which carbon dioxide is dissolved to be condensed as the relative humidity within the cathode region exceeds 100% and forms a water film on the cathode surface; and using the carbon dioxide dissolved in the water film as a reactant. The present invention is based on the above findings.

As described above, the method according to the present invention of preparing a reduction product of carbon dioxide by electrochemically reducing carbon dioxide within an electrochemical cell, which includes an anode, a cathode, and an electrolyte membrane which is disposed between the anode and the cathode to separate the anode region and the cathode region, and has a first temperature, includes:

(1) supplying water or an electrolytic solution to the anode region;

(2) supplying a carbon dioxide gas which has been humidified in a condition where the relative humidity exceeds 100% by supplying a humidified carbon dioxide gas having a second temperature higher than a first temperature to the cathode region within the electrochemical cell having the first temperature; and (3) applying a voltage between the anode region and the cathode region to generate hydrogen ions ($H^+$) in the anode region, in which the hydrogen ions move to the cathode region through the electrolyte membrane and thereby electrochemically reduce the carbon dioxide gas so as to produce a reduction product of carbon dioxide.

Additionally, as described above, the apparatus of preparing a reduction product of carbon dioxide by electrochemically reducing carbon dioxide according to the present invention includes:

an electrochemical cell, which includes an anode; a cathode; and an electrolyte membrane which is disposed between the anode and the cathode to separate the anode region and the cathode region; an inlet of supplying water or an electrolytic solution to the anode region; and an inlet of supplying humidified carbon dioxide to the cathode region;

an energy supply source, which is operably linked to the anode and the cathode, and which applies a voltage between the anode and the cathode to reduce the carbon dioxide in the cathode to a reduction product of the carbon dioxide; and a humidifier or atomizer, which is linked to the inlet for supplying humidified carbon dioxide to the cathode region, and thereby supplies humidified carbon dioxide to the cathode region, in which water or an electrolytic solution is supplied to the anode region; a carbon dioxide gas which has been humidified in a condition where the relative humidity exceeds 100% is supplied by supplying a humidified carbon dioxide gas having a second temperature higher than a first temperature to the cathode region within the electrochemical cell having the first temperature; and a voltage is applied between the anode and the cathode to generate hydrogen ions ($H^+$) in the anode region, the hydrogen ions are transported to the cathode region through the electrolyte membrane, and thereby the carbon dioxide gas is electrochemically reduced and a reduction product of carbon dioxide is produced.

The electrochemical carbon dioxide conversion reaction is a reaction in which carbon dioxide is reduced to a useful carbon compound through electron transfer by generating a potential difference between the two electrodes by applying electrical energy. The present invention provides a method and apparatus of preparing a reduction product of carbon dioxide by electrochemical reduction of carbon dioxide as an electrochemical carbon dioxide conversion reaction.

In the present invention, the reduction product of carbon dioxide may be formic acid, formaldehyde, formate, acetaldehyde, acetate, acetic acid, acetone, 1-butanol, 2-butanol, 2-butanone, ethanol, isopropanol, lactate, lactic acid, methanol, 1-propanal, 1-propanol, propionic acid, or a mixture thereof.

In the present invention, as an electrochemical carbon dioxide conversion system, an electrochemical reaction system enabling a gas-phase reaction can be used, e.g., a fuel cell.

The electrochemical cell used in the present invention includes an anode, a cathode, and an electrolyte membrane which is located between the anode and the cathode and separates the anode region and the cathode region, and has a first temperature.

In the present invention, the electrochemical cell may include a membrane-electrode assembly having an anode catalyst layer and a cathode catalyst layer formed on each surface of the electrolyte membrane, respectively, and a gas diffusion layer for supplying the humidified carbon dioxide to the catalyst layers formed in the cathode side of the membrane-electrode assembly.

The anode is an oxidizing electrode in which water molecules are oxidized to generate oxygen ($O_2$) gas, hydrogen ions ($H^+$), and electrons ($e^-$). In particular, the hydrogen ions generated move through the electrolyte membrane and the electrons move along the external circuit to the cathode, that is, the reducing electrode. At the cathode, the electrons and hydrogen ions which moved from the anode meet with carbon dioxide and cause a reduction reaction. In the reduction electrode, the electrons and hydrogen ions which moved from the oxidizing electrode meet with carbon dioxide to cause a reduction reaction, and various conversion products are generated depending on the number of the electrons and hydrogen ions participating in the reaction.

For the anode catalyst layer, Pt, Au, Pd, Ir, Ag, Rh, Ru, Ni, Al, Mo, Cr, Cu, Ti, W, alloys thereof, or mixed metal oxides (e.g., $Ta_2O_5$, $IrO_2$, etc.) may be used.

Since the carbon dioxide reduction reaction competes with the hydrogen generation reaction, it is preferable to use a catalyst having a large overvoltage in the hydrogen generation reaction and exhibiting activity in the carbon dioxide reduction reaction as the cathode material.

For the cathode catalyst layer, any one selected from the group consisting of Sn, a Sn alloy, Al, Au, Ag, C, Cd, Co, Cr, Cu, a Cu alloy, Ga, Hg, In, Mo, Nb, Ni, $NiCo_2O_4$, a Ni alloy, a Ni—Fe alloy, Pb, Rh, Ti, V, W, Zn, Elgiloy® (an alloy in accordance with ASTM F 1058), nichrome, austenitic steel, duplex steel, ferrite steel, martensitic steel, stainless steel, degenerately-doped p-Si, degenerately doped p-Si:As, degenerately-doped p-Si:B, degenerately-doped n-Si, degenerately-doped n-Si:As, degenerately-doped n-Si:B, and mixtures thereof may be used. As the Sn alloy, preferably, Sn—Pb may be used.

In the present invention, as the relative humidity in the cathode region exceeds 100%, the water in which carbon dioxide is dissolved is condensed on the cathode surface and forms a water film, and since a reduction product is produced by electrochemical reduction using the carbon dioxide dissolved therein, as shown in FIG. 2, the cathode may include an electrode catalyst located on the cathode region side of the electrolyte membrane and a gas diffusion layer (e.g., carbon paper) capable of uniformly supplying humidified carbon dioxide gas, and the electrode catalyst may have various structures (e.g., particles, a porous structure) and surface properties to facilitate the water-film formation on the cathode surface.

As the electrolyte membrane, a cation exchange membrane (CEM) or anion exchange membrane (AEM), for example, Nafion® N115, etc., may be used.

Step (1) relates to supplying water or an electrolytic solution to the anode region to generate hydrogen ions ($H^+$) through oxidation of water molecules. That is, water or an electrolytic solution containing water may be supplied to the anode region to induce oxidation of water molecules.

The electrolytic solution is an aqueous solution which contains $KHCO_3$, $K_2CO_3$, $KOH$, $KCl$, $KClO_4$, $K_2SiO_3$, $Na_2SO_4$, $NaNO_3$, $NaCl$, $NaF$, $NaClO_4$, $CaCl_2$, guanidinium cations, $H^+$ ions, alkali metal cations, ammonium cations, alkylammonium cations, halide ions, alkylamines, borates, carbonates, guanidinium derivatives, nitrites, nitrates, phosphates, polyphosphates, perchlorates, silicates, sulfates, tetraalkylammonium salts, or a mixture thereof as an electrolyte, but the electrolyte is not limited thereto.

Step (2) relates to supplying a carbon dioxide gas while providing a condition where the relative humidity exceeds 100% by supplying humidified carbon dioxide gas having a second temperature higher than a first temperature to the cathode region within the electrochemical cell having the first temperature.

As used herein, the term "first temperature", which is a temperature within an electrochemical cell, may specifically refer to a temperature of a cathode region within the electrochemical cell. For example, the first temperature may be in the range of 10° C. to 120° C., preferably 25° C. to 80° C.

As used herein, the term "second temperature" refers to a temperature of humidified carbon dioxide gas supplied to a cathode region, and it suffices as long as the second temperature is higher than the first temperature. Specifically, the second temperature may be in the range of 30° C. to 150° C., for example, 35° C. to 130° C.

In the present invention, a reduction reaction of carbon dioxide to a reduction product with high Faradaic efficiency can be performed in an environment substantially similar to that of a liquid-phase reaction, by allowing the water in which carbon dioxide is dissolved to be condensed and form a water film on the cathode surface by making the relative humidity within the cathode region exceed 100% by supplying humidified carbon dioxide gas, which has a temperature higher than the cathode region where the reduction reaction of carbon dioxide occurs, followed by inducing a reduction reaction using the carbon dioxide dissolved in the water film as a reactant.

In the present invention, it suffices that the relative humidity in step (2) exceeds 100%, and specifically, the relative humidity may be in the range of 150% to 2,000%.

Step (3) relates to producing a reduction product of carbon dioxide by applying a voltage between the anode region and the cathode region, followed by electrochemically reducing the carbon dioxide gas.

In producing a reduction product of carbon dioxide from carbon dioxide by an electrochemical reduction reaction, formal potentials (mV vs. NHE. pH=7) are as follows.

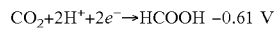

$CO_2+2H^++2e^-\rightarrow HCOOH$  $-0.61$ V

$CO_2+4H^++4e^-\rightarrow HCHO+H_2O$  $-0.48$ V

$CO_2+6H^++6e^-\rightarrow CH_3OH+H_2O$  $-0.38$ V

In fact, the reduction reaction of carbon dioxide may proceed at a more negative potential than the potential shown above because the reduction reaction of carbon dioxide does not readily occur and requires a large overvoltage. In the present invention, a voltage may be applied so as to generate a potential, at which the reduction reaction can occur, by adding a more negative potential than the formal potential. For example, a voltage of 1.6 V or greater, for example, a voltage of 4 V or greater, and specifically, a voltage of 4 V or 6 V may be applied.

A desired reduction product of carbon dioxide can be obtained by controlling a cathode, electrolyte, and/or potential. Specifically, Sn, Pb, a Sn alloy (e.g., Sn—Pb alloy), In, Hg, etc. may be used as the cathode for the production of formic acid and/or formate; and additionally, Cu may be used for the production of formaldehyde, acetaldehyde, acetate, acetic acid, acetone, 1-butanol, 2-butanol, 2-butanone, ethanol, isopropanol, lactate, lactic acid, methanol, 1-propanal, 1-propanol, and/or propionic acid.

In step (3), the carbon dioxide in the water, which has been condensed from humidified carbon dioxide gas, is reduced as the relative humidity exceeds 100% and thereby a reduction product of carbon dioxide is produced, and thus, the reduction product of carbon dioxide is produced in the form of an aqueous solution. In particular, some water which has undergone a crossover in the anode region may be added to the condensed water during the carbon dioxide reduction and thereby further promote spontaneous reduction of carbon dioxide. Since the amount of water that undergoes a crossover is limited relative to the conventional liquid-phase reaction, the concentration of the reduction product of carbon dioxide is not excessively diluted.

That is, the carbon dioxide supplied in a gaseous state as such is reduced in a small amount of liquid-phase water, and thus a reduction product of carbon dioxide can be obtained at a higher concentration than the conventional liquid reaction.

In the present invention, the concentration of the reduction product of carbon dioxide produced in step (3) may be in the range of 1% (w/v) to 20% (w/v). Specifically, in an embodiment of the present invention, it was confirmed that the reduction product of carbon dioxide having a concentration of 1.4% (w/v) to 8.3% (w/v) at a relative humidity of 100% or higher, and more specifically, having a concentration of 1.4% (w/v) to 7% (w/v) at a relative humidity of 300% to 1,500% can be produced in an aqueous solution.

Additionally, as described above, the present invention can perform the reduction reaction of carbon dioxide with a Faradaic efficiency of 80% or higher because the present invention can further promote the spontaneous reduction reaction of carbon dioxide in a liquid-like environment by providing a minimal amount of water due to the condensation of oversaturated water and subsequent formation of a water film on the surface of the cathode as the relative humidity exceeds 100% in step (3). That is, the reduction product of carbon dioxide can be produced to have a Faradaic efficiency of 80% or higher in step (3).

As used herein, the term "Faradaic efficiency" may refer to the efficiency with which charge (electrons) transfers in a system that performs electrochemical reactions, and is also referred to as "Faradaic yield", "Coulombic efficiency", or "current efficiency". The Faradaic efficiency can be obtained by comparing a stoichiometric amount of the starting material converted to the product by the applied current with the amount of the product actually measured. That is, in the present invention, the Faradaic efficiency can refer to the conversion efficiency of carbon dioxide to reduction product of carbon dioxide due to the applied current.

Advantageous Effects of the Invention

The method of preparing a reduction product of carbon dioxide by a reduction reaction of carbon dioxide according to the present invention can prepare, in an energy-efficient manner, the high-concentration reduction product of carbon dioxide with high Faraday efficiency, as in a liquid-phase reduction reaction, by producing the reduction product of carbon dioxide by supplying water or an electrolytic solution to an anode region; supplying humidified carbon dioxide gas having a second temperature higher than a first temperature to a cathode region within an electrochemical cell having the first temperature, so as to supply the carbon dioxide gas which has been humidified to be in a condition where the relative humidity is greater than 100%, while applying a voltage between the anode region and the cathode region so as to generate hydrogen ions ($H^+$) in the anode region; and transporting the hydrogen ions to the cathode region through the electrolyte membrane, thereby electrochemically reducing the carbon dioxide gas.

BRIEF DESCRIPTION OF DRAWINGS

FIGS. 1A and 1B are schematic diagrams that thermodynamically explain the limit of the existing gas-phase reduction reaction of carbon dioxide.

FIG. 2 is a conceptual diagram schematically illustrating the reduction reaction of carbon dioxide occurring in an apparatus and each part of the apparatus according to an embodiment of the present invention.

FIG. 3 is a schematic conceptual diagram of an apparatus of preparing formic acid (HCOOH) by electrochemically reducing carbon dioxide ($CO_2$) according to an embodiment of the present invention.

FIG. 4 shows the measurement results of Faradaic efficiency according to relative humidity in preparing formic acid (HCOOH) by electrochemical reduction of carbon dioxide ($CO_2$) according to the method of the present invention.

FIG. 5 shows the measurement results of recovery rate of liquid-phase products according to relative humidity in preparing formic acid by electrochemical reduction of carbon dioxide according to the method of the present invention.

FIG. 6 shows the measurement results of current density according to relative humidity in preparing formic acid by electrochemical reduction of carbon dioxide according to the method of the present invention.

FIG. 7 shows the measurement results of concentration of formic acid production according to relative humidity in preparing formic acid by electrochemical reduction of carbon dioxide according to the method of the present invention.

BEST MODE

Preferred embodiments of the present invention will be described in detail with reference to the accompanying drawings so that those skilled in the art can easily carry out the present invention Hereinafter, a configuration of an apparatus of preparing a reduction product of carbon dioxide ($CO_2$) (e.g., formic acid (HCOOH)) by electrochemically reducing carbon dioxide according to an embodiment of the present invention will be described.

FIG. 3 is a schematic conceptual diagram of an apparatus of preparing a reduction product of carbon dioxide (e.g., formic acid (HCOOH)) by electrochemically reducing carbon dioxide according to an embodiment of the present invention.

Referring to FIG. 3, the apparatus of preparing a reduction product of carbon dioxide by electrochemically reducing carbon dioxide according to an embodiment of the present invention may include:

an electrochemical cell, which includes an anode; a cathode; and an electrolyte membrane which is disposed between the anode and the cathode to separate the anode region and the cathode region; an inlet for supplying water or an electrolytic solution to the anode region; and an inlet for supplying humidified carbon dioxide to the cathode region;

an energy supply source, which is operably linked to the anode and the cathode through current collector, and applies a voltage between the anode and the cathode to reduce the carbon dioxide in the cathode to a reduction product of the carbon dioxide; and a humidifier or atomizer, which is linked to the inlet for supplying humidified carbon dioxide to the cathode region and thereby supplies humidified carbon dioxide to the cathode region.

The energy supply source may be configured in such a manner that the energy supply source is operably linked to the anode and the cathode, and applies a voltage between the anode and the cathode to reduce the carbon dioxide to the reduction product of carbon dioxide in the cathode.

The electrical energy for the electrochemical reduction of carbon dioxide may come from conventional energy supply sources, including conventional nuclear energy sources and alternative energy supply sources from solar cells or other non-fossil fuel electricity sources (e.g., hydro power, wind power, solar power generation, geothermal, etc.). Preferably, the electricity source can supply a voltage higher than 1.6 V across the cell. Adjustment to different voltage values may be made depending on the internal resistance of the cell used.

In the above apparatus, hydrogen ions ($H^+$) can be generated as shown in Reaction Scheme 1 below when water or an electrolytic solution is supplied to the anode region and current is applied.

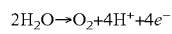  [Reaction Scheme 1]

That is, the reactant in the anode is in a liquid phase in the present invention. As described above, in the anode region, hydrogen ions ($H^+$) can be generated by supplying only water, and hydrogen ions ($H^+$) can also be generated even by supplying an electrolytic solution, specifically an aqueous solution containing an electrolyte. The electrolytic solution may be an aqueous electrolytic solution at a concentration of 0.1 M to 1 M.

On the other hand, carbon dioxide gas can be electrochemically reduced to formic acid by hydrogen cations ($H^+$) that have moved to the cathode region through the electrolyte membrane as shown in Reaction Scheme 2 below, under conditions where relative humidity exceeds 100%, by supplying humidified carbon dioxide gas having a second temperature higher than a first temperature to the cathode region within the electrochemical cell having the first temperature.

$$2CO_2 + 4H^+ + 4e^- \rightarrow 2HCOOH$$ [Reaction Scheme 2]

That is, the reactant in the cathode region is $CO_2$ gas which is humidified to be in a condition where the relative humidity exceeds 100%, that is, in a gaseous phase.

Relative humidity is defined as follows, and thus relative humidity can be adjusted via the temperature of the electrochemical cell and the temperature of the humidifier or atomizer.

Relative humidity=(Saturated water vapor pressure at a temperature within a humidifier or atomizer/ Saturated water vapor pressure at a temperature inside of a cell)×100(%)

That is, excess water can be supplied to the electrochemical cell, specifically to the cathode region, with the reactant (i.e., $CO_2$) by passing the $CO_2$ gas by setting the temperature of the humidifier or atomizer at a temperature higher than that of the electrochemical cell. In particular, the water supplied in excess is condensed and forms a water film on the surface of the electrode (i.e., the cathode) and the reaction proceeds easily as in a liquid-phase reaction because the $CO_2$ supplied together with the water is dissolved in the condensed water film and used as a reactant. Additionally, $CO_2$ (i.e., the reactant) is delivered to the surface of the electrode (i.e., the cathode) in a gaseous phase, and the $CO_2$ consumed by the reaction in the water film is constantly replenished by the $CO_2$ gas being supplied, and thus it is possible to minimize mass transfer resistance without being limited by solubility.

Additionally, since the activation energy of the reaction is lowered using a minimum amount of water, the formic acid being produced can be recovered at a high concentration. Accordingly, the cost required for separation, purification, and concentration can be reduced.

In Example of the present invention, it was confirmed that highly-concentrated formic acid in the range of 1.4% (w/v) to 8.3% (w/v) (i.e., 14,000 ppm to 83,000 ppm in terms of ppm) can be recovered with a Faradaic efficiency of 80% or higher when humidified $CO_2$ gas having a relative humidity of 100% or higher is supplied to the cathode region. More specifically, it was confirmed that highly-concentrated formic acid in the range of 1.4% (w/v) to 7% (w/v) (i.e., 14,000 ppm to 70,000 ppm in terms of ppm) can be recovered with a Faradaic efficiency of 80% or higher when the humidified $CO_2$ gas having a relative humidity of 300% to 1,500% is supplied to the cathode region.

Additionally, since an aqueous solution is supplied to the anode region, the water that undergoes a crossover in the anode region is supplied to the cathode region and thereby more spontaneously promotes the electrochemical reduction reaction of carbon dioxide, and thus it is possible to recover highly-concentrated formic acid with much greater efficiency. Furthermore, the highly-concentrated formic acid can be purified using a gas/liquid separation apparatus as shown in FIG. 3.

Hereinafter, the method of preparing formic acid using an apparatus of preparing formic acid (HCOOH) by electrochemically reducing the carbon dioxide ($CO_2$) according to the present invention will be described in more detail with reference to the following Examples. However, these Examples are for illustrative purposes only and the invention is not limited by these Examples.

Example 1: Preparation of Apparatus of Preparing Formic Acid by Electrochemically Reducing Carbon Dioxide As shown in FIGS. 2 and 3, an apparatus of preparing formic acid (HCOOH) by electrochemically reducing carbon dioxide ($CO_2$) according to an embodiment of the present invention was prepared.

The catalysts used for the anode and the cathode were platinum (Pt) and tin (Sn), respectively, and particulate metal catalyst powders were mixed and dispersed in an alcohol together with a Nafion ionomer, which served as a binder, and the resultant was coated on each side of an electrolyte membrane to form an electrode catalyst layer, and thereby a membrane-electrode assembly was prepared. In order to smoothly supply humidified $CO_2$ to the catalyst layer, a carbon paper layer having a thickness of 0.1 mm to 0.5 mm was used as a gas diffusion layer in the cathode side of the prepared membrane electrode assembly. A current collector was inserted into both sides of a membrane-electrode assembly including the gas diffusion layer so as to allow a current to flow between the two electrodes when a voltage is applied thereto, and a flow path was formed to supply reactants and release products.

Experimental Example 1: Examination of Efficiency of Method for Preparing Formic Acid According to the Present Invention The performance of formic acid preparation was evaluated at a relative humidity of 100% to 1,500% by varying the humidifier temperature where the internal temperature of the cell was set at 25° C., using the apparatus of preparing formic acid (HCOOH) by electrochemically reducing carbon dioxide ($CO_2$) prepared in Example 1.

In particular, the experimental conditions were as follows and the humidification conditions were as shown in Table 1:

Reaction voltage: 3 V (constant voltage operation)
Reaction temperature: 298 K
Reaction pressure: 1 atm (atmospheric pressure)
Electrolyte membrane: Nafion 115
Anode catalyst: Pt black
Cathode catalyst: Sn powder
Electrode area: 25 cm²
Anode reactant: aqueous solution of 0.5 M $KHCO_3$ 40 mL/min
Cathode reactant: humidified $CO_2$ gas 300 mL/min (relative humidity 100% to 1,500%)

TABLE 1

| Relative Humidity (%) | Internal Temperature of Cell (° C.) | Humidifier Temperature (° C.) |
|---|---|---|
| 100 | 25 | 25 |
| 300 | 25 | 45 |
| 700 | 25 | 63 |
| 1000 | 25 | 71 |
| 1500 | 25 | 80 |

The results are shown in FIGS. 4 to 7.

FIG. 4 shows the measurement results of Faradaic efficiency according to relative humidity. In FIG. 4, it was confirmed that formic acid can be produced at a Faradaic efficiency of 80% or higher under the condition where relative humidity exceeds 100% using the method according to the present invention.

FIG. 5 shows the measurement results of recovery rate of liquid-phase products according to relative humidity. In FIG. 5, it was confirmed that formic acid can be produced at a recovery rate of 1 mL/h to 10 mL/h under the condition where relative humidity exceeds 100% using the method according to the present invention.

FIG. 6 shows the measurement results of current density according to relative humidity. In FIG. 6, it was confirmed that the current density slightly increases as the relative humidity increases.

FIG. 7 shows the measurement results of concentration of formic acid produced according to relative humidity. In FIG. 7, it was confirmed that highly-concentrated formic acid can be produced at a concentration of 1.4% (w/v) to 8.3% (w/v) under the condition where relative humidity exceeds 100% using the method according to the present invention.

The invention claimed is:

1. An apparatus of preparing a reduction product of carbon dioxide ($CO_2$) by electrochemically reducing carbon dioxide, comprising:
   an electrochemical cell, which comprises:
   an anode;
   a cathode;
   an electrolyte membrane which is disposed between the anode and the cathode to separate the anode region and the cathode region, and is configured to transport hydrogen ions ($H^+$) from the anode to the cathode region therethrough;
   an inlet configured to supply water or an electrolytic solution to the anode region; and
   an inlet configured to supply humidified carbon dioxide to the cathode region;
   an energy supply source, which is operably linked to the anode and the cathode, and is configured to apply a voltage between the anode and the cathode to generate hydrogen ions in the anode region and reduce the carbon dioxide in the cathode to produce a reduction product of the carbon dioxide; and
   a humidifier or atomizer, which is linked to the inlet for supplying humidified carbon dioxide to the cathode region, and is configured to humidify carbon dioxide so that humidified carbon dioxide having the relative humidity in a range of 150% to 2,000% is supplied to the cathode region within the electrochemical cell.

2. The apparatus of claim 1, wherein, upon applying a voltage, the moisture in which carbon dioxide is dissolved is condensed as the relative humidity within the cathode region is in a range of 150% to 2,000% and forms a water film on the cathode surface, and the reduction product is produced from the carbon dioxide dissolved in the water film as a reactant by electrochemical reduction.

3. The apparatus of claim 1, wherein the electrochemical cell comprises a membrane-electrode assembly having an anode catalyst layer and a cathode catalyst layer formed on each surface of the electrolyte membrane, respectively, wherein a gas diffusion layer of supplying the humidified carbon dioxide to the catalyst layer, which is placed in the cathode side of the membrane-electrode assembly.

4. The apparatus of claim 1, wherein the electrochemical cell has a first temperature, and the supply of the carbon dioxide gas which has been humidified in a condition where the relative humidity is in a range of 150% to 2,000% is achieved by providing a humidified carbon dioxide gas having a second temperature higher than the first temperature to the cathode region within the electrochemical cell.

5. The apparatus of claim 1, wherein the relative humidity is in a range of 300% to 1,500%.

6. A method of preparing a reduction product of carbon dioxide ($CO_2$) by electrochemically reducing carbon dioxide within an electrochemical cell, which comprises an anode, a cathode, and an electrolyte membrane which is disposed between the anode and the cathode to separate the anode region and the cathode region:
   (1) supplying water or an electrolytic solution to the anode region;
   (2) supplying a carbon dioxide gas, which has been humidified by using a humidifier or atomizer in a condition where the relative humidity is in a range of 150% to 2,000%, to the cathode region within the electrochemical cell; and
   (3) applying a voltage between the anode region and the cathode region to generate hydrogen ions ($H^+$) in the anode region, wherein the hydrogen ions move through the electrolyte membrane to the cathode region and then electrochemically reduce the carbon dioxide gas so as to produce a reduction product of carbon dioxide.

7. The method of claim 6, wherein, upon applying a voltage in step (3), the moisture in which carbon dioxide is dissolved is condensed as the relative humidity within the cathode region is in a range of 150% to 2,000% and forms a water film on the cathode surface, and the reduction product is produced from the carbon dioxide dissolved in the water film as a reactant by electrochemical reduction.

8. The method of claim 6, wherein the electrochemical cell comprises a membrane-electrode assembly having an anode catalyst layer and a cathode catalyst layer formed on each surface of the electrolyte membrane, respectively, and a gas diffusion layer of supplying the humidified carbon dioxide to the catalyst layer, which is placed in the cathode side of the membrane-electrode assembly.

9. The method of claim 6, wherein the reduction product of the carbon dioxide is formic acid, formaldehyde, formate, acetaldehyde, acetate, acetic acid, acetone, 1-butanol, 2-butanol, 2-butanone, ethanol, isopropanol, lactate, lactic acid, methanol, 1-propanal, 1-propanol, propionic acid, or a mixture thereof.

10. The method of claim 6, wherein a first temperature of the electrochemical cell is in the range of 10° C. to 25° C.

11. The method of claim 6, wherein a second temperature of the humidified carbon dioxide gas is in the range of 30° C. to 100° C.

12. The method of claim 6, wherein the reduction product of the carbon dioxide in step (3) is dissolved in the water derived from the humidified carbon dioxide gas and water which has undergone a crossover from the anode region, and produced in the form of an aqueous solution.

13. The method of claim 6, wherein the reduction product of the carbon dioxide produced in step (3) has a concentration of 1% (w/v) to 20% (w/v).

14. The method of claim 6, wherein the reduction product of the carbon dioxide in step (3) is produced with a Faradaic efficiency of 80% or higher.

15. The method of claim 6, wherein the cathode is selected from the group consisting of Sn, a Sn alloy, Al, Au, Ag, C, Cd, Co, Cr, Cu, a Cu alloy, Ga, Hg, In, Mo, Nb, Ni, $NiCo_2O_4$, a Ni alloy, a Ni—Fe alloy, Pb, Rh, Ti, V, W, Zn, an alloy in accordance with ASTM F 1058, nichrome, austenitic steel, duplex steel, ferrite steel, martensitic steel, stainless steel, degenerately-doped p-Si, degenerately doped p-Si:As, degenerately-doped p-Si:B, degenerately-doped n-Si, degenerately-doped n-Si:As, degenerately-doped n-Si:B, and mixtures thereof.

16. The method of claim 15, wherein the Sn alloy as the cathode is a Sn—Pb alloy.

17. The method of claim 6, wherein the electrolytic solution is an aqueous solution comprising an electrolyte of $KHCO_3$, $K_2CO_3$, KOH, KCl, $KClO_4$, $K_2SiO_3$, $Na_2SO_4$, $NaNO_3$, NaCl, NaF, $NaClO_4$, $CaCl_2$), guanidinium cations, $H^+$ ions, alkali metal cations, ammonium cations, alkylammonium cations, halide ions, alkylamines, borates, carbonates, guanidinium derivatives, nitrites, nitrates, phosphates, polyphosphates, perchlorates, silicates, sulfates, tetraalkylammonium salts, or a mixture thereof.

18. The method of claim 6, wherein the electrochemical cell has a first temperature, and the supply of the carbon dioxide gas which has been humidified in a condition where the relative humidity is in a range of 150% to 2,000% in the step (2) is achieved by providing a humidified carbon dioxide gas having a second temperature higher than the first temperature to the cathode region within the electrochemical cell.

* * * * *